(12) United States Patent
Yamawaki

(10) Patent No.: US 9,526,688 B2
(45) Date of Patent: Dec. 27, 2016

(54) WATER-BASED LIQUID COSMETIC

(71) Applicant: TOKIWA CORPORATION, Nakatsugawa-shi, Gifu (JP)

(72) Inventor: Yuka Yamawaki, Kawaguchi (JP)

(73) Assignee: TOKIWA CORPORATION (JP)

( * ) Notice: Subject to any disclaimer, the term of this patent is extended or adjusted under 35 U.S.C. 154(b) by 0 days.

(21) Appl. No.: 14/960,485

(22) Filed: Dec. 7, 2015

(65) Prior Publication Data
US 2016/0199285 A1 Jul. 14, 2016

(30) Foreign Application Priority Data

Jan. 8, 2015 (JP) .................................. 2015-002338

(51) Int. Cl.
*A61K 31/74* (2006.01)
*A61K 31/00* (2006.01)
*A61K 8/85* (2006.01)
*A61K 8/81* (2006.01)
*A61Q 1/10* (2006.01)
*A61K 8/39* (2006.01)
*A61K 8/73* (2006.01)
*A61K 8/86* (2006.01)

(52) U.S. Cl.
CPC . *A61K 8/85* (2013.01); *A61K 8/39* (2013.01); *A61K 8/731* (2013.01); *A61K 8/8152* (2013.01); *A61K 8/8158* (2013.01); *A61K 8/8176* (2013.01); *A61K 8/86* (2013.01); *A61Q 1/10* (2013.01); *A61K 2800/594* (2013.01)

(58) Field of Classification Search
None
See application file for complete search history.

(56) References Cited

U.S. PATENT DOCUMENTS

2010/0086507 A1* 4/2010 Gueret .................. A45D 40/26
424/70.7

FOREIGN PATENT DOCUMENTS

| JP | 2002-241233 A | 8/2002 |
| JP | 2007-153744 A | 6/2007 |
| JP | 2009-161442 A | 7/2009 |
| JP | 2011-213633 A | 10/2011 |

* cited by examiner

Primary Examiner — Robert A Wax
Assistant Examiner — Quanglong Truong
(74) Attorney, Agent, or Firm — Bacon & Thomas, PLLC

(57) ABSTRACT

[Object] Provided is a water-based liquid cosmetic which exhibits excellent usability such as density of drawn line and convenience of drawing as well as can discharge a sufficient amount of liquid even when being formed into an automatic pen type, and also can form a cosmetic film exhibiting both lasting properties and washability.

[Solving Means] The water-based liquid cosmetic according to the present invention is a water-based liquid cosmetic which includes a film-forming agent, a coloring pigment, and water, in which a sulfonated polyester (A) and a polymer (B) containing an alkyl (meth)acrylate monomer as a constitutional unit are contained at from 2 to 11% by mass and from 2 to 18% by mass with respect to a total amount of the cosmetic, respectively, as the film-forming agent.

5 Claims, No Drawings

US 9,526,688 B2

WATER-BASED LIQUID COSMETIC

TECHNICAL FIELD

The present invention relates to a water-based liquid cosmetic.

BACKGROUND ART

As make-up cosmetics such as eyeliner, eyebrow, mascara, those using liquid cosmetics are known. These make-up cosmetics have a cosmetic effect that an eye is made clear and the pupil of eye looks bigger when being applied to the edge of the eye. The liquid cosmetics to be used in such an application are required to have usability such as excellent coloring and smoothness or ease of drawing at the time of application, and retention of the cosmetic effect such as water resistance, prevention of bleeding, prevention of the secondary attachment, and stability of the applied film over time.

As the liquid cosmetics exhibiting water resistance among the required properties, oil-based liquid cosmetics are known (for example, the following Patent Document 1). As the liquid cosmetics exhibiting usability such as ease of drawing, water-based liquid cosmetics are known (for example, the following Patent Document 2). As the liquid cosmetics exhibiting water resistance and smooth usability, water-in-oil liquid cosmetics are known (for example, the following Patent Document 3). Although the types of the liquid cosmetics are diverse as described above, water-based liquid cosmetics tend to be preferred from the viewpoint of usability such as smoothness or ease of drawing at the time of application.

However, it is difficult to improve the coloring property or the retention of the cosmetic effect of water-based liquid cosmetics. There is a problem of water resistance when using a water-soluble dye that is highly soluble in water as a coloring agent, and color unevenness is easily caused when using a pigment such as black iron oxide or carbon black since it is difficult to uniformly disperse the pigment in the water-based liquid cosmetic. In addition, water-based liquid cosmetics have a problem that it is difficult to impart high lasting properties (water resistance, sebum resistance, and rub resistance) that bleeding of the water-based liquid cosmetic by moisture such as tears or sebum or peeling off of the cosmetic film can be prevented.

With regard to the lasting properties of water-based liquid cosmetics, for example, a technique is proposed in the following Patent Document 4 that high rub resistance is obtained by a strong cosmetic film formed of a film-forming agent such as alkyl acrylate copolymer emulsion (for example, the following Patent Document 4).

CITATION LIST

Patent Document

Patent Document 1: JP 2011-213633 A
Patent Document 2: JP 2002-241233 A
Patent Document 3: JP 2009-161442 A
Patent Document 4: JP 2007-153744 A

SUMMARY OF THE INVENTION

Problem to be Solved by the Invention

However, the make-up cosmetics are required to have washability that the cosmetic film can be easily washed out when washing the applied cosmetic as well as to have improved lasting properties. A further improvement is desired in order to satisfy these contradictory properties at a high level even in the prior art.

Incidentally, as the product form of liquid cosmetics, a bottle type to directly fill the cosmetic in a container, an automatic pen type to discharge the cosmetic, or the like is known. The automatic pen type cosmetics are equipped with a fiber bundle impregnated with a cosmetic or a filling portion filled with a cosmetic and an applying portion, and the cosmetic is discharged by the action of surface tension of the liquid cosmetic and capillary phenomenon. The automatic pen type cosmetics tend to be preferred from the viewpoint of a convenience of usage or portability, and the water-based liquid cosmetics are excellently compatible with the automatic pen type. However, when the viscosity of the liquid cosmetic to be impregnated or filled is too high, the discharge amount is insufficient for the reasons that the liquid cosmetic does not sufficiently move to the applying portion such as a pen tip or is clogged up at the applying portion, and thus writing properties tend to deteriorate. On the other hand, when the viscosity of the liquid cosmetic is too low, a problem is easily caused that the liquid cosmetic is bleeding when being applied to the skin, the cosmetic is leaking (liquid leakage) from the fiber bundle or the applying portion, or the like.

The invention has been achieved in view of the above circumstances, and an object thereof is to provide a water-based liquid cosmetic which exhibits excellent usability such as density of drawn line and convenience of drawing as well as can discharge a sufficient amount of liquid even when being formed into an automatic pen type, and also can form a cosmetic film exhibiting both lasting properties and washability.

Means for Solving Problem

In order to achieve the above object, the invention provides a water-based liquid cosmetic which includes a film-forming agent, a coloring pigment, and water, in which a sulfonated polyester (A) and a polymer (B) containing an alkyl (meth)acrylate monomer as a constitutional unit are contained at from 2 to 11% by mass and from 2 to 18% by mass with respect to a total amount of the cosmetic, respectively, as the film-forming agent.

Incidentally, in the present specification, the content of the film-forming agent in the water-based liquid cosmetic refers to the value of the film-forming agent in terms of solid content.

According to the water-based liquid cosmetic of the invention, excellent usability such as density of drawn line and convenience of drawing is exhibited as well as a sufficient amount of liquid can be discharged even when being formed into an automatic pen type, and also a cosmetic film exhibiting both lasting properties and washability can be formed by having the above configuration.

It is preferable that the water-based liquid cosmetic of the invention contains a sulfonated copolyester of isophthalic acid as the component (A) from the viewpoint of washability of the cosmetic film.

In addition, it is preferable that the water-based liquid cosmetic of the invention contains one or more kinds of an alkyl acrylate-styrene copolymer, an alkyl acrylate copolymer, or an alkyl acrylate-diacetone acrylamide copolymer as the component (B) from the viewpoint of rub resistance, water resistance, and sebum resistance.

Effect of the Invention

According to the invention, it is possible to provide a water-based liquid cosmetic which exhibits excellent usability such as density of drawn line and convenience of drawing as well as can discharge a sufficient amount of liquid even when being formed into an automatic pen type, and also can form a cosmetic film exhibiting both lasting properties and washability.

MODE(S) FOR CARRYING OUT THE INVENTION

The water-based liquid cosmetic according to the present embodiment includes a film-forming agent, a coloring pigment, and water, and includes a sulfonated polyester (A) (hereinafter, referred to as the component (A) in some cases) and a polymer (B) (hereinafter, referred to as the component (B) in some cases) containing an alkyl (meth)acrylate monomer as a constitutional unit at from 2 to 11% by mass and from 2 to 18% by mass with respect to a total amount of the cosmetic, respectively, as the film-forming agent.

According to the water-based liquid cosmetic according to the present embodiment, it is possible to form a cosmetic film which exhibits both lasting properties and washability at a level that cannot be achieved by blending a single film-forming agent by concurrently using the specific film-forming agents at the specific proportions. In addition, according to the water-based liquid cosmetic of the present embodiment, it is possible to form a cosmetic film which exhibits sufficient water resistance even when a dispersant to disperse the coloring pigment is blended so as to obtain a sufficient density of drawn line without color unevenness. Furthermore, according to the water-based liquid cosmetic according to the present embodiment, it is possible to adjust the viscosity to a value at which both a sufficient discharge amount and the prevention of bleeding and liquid dripping can be achieved in the case of forming the water-based liquid cosmetic into an automatic pen type.

The sulfonated polyester of the component (A) refers to a polyester containing a sulfur atom, such as a sulfo group (for example, $-SO_3$ group). Examples of the structure derived from a dicarboxylic acid constituting the sulfonated polyester may include isophthalic acid and sulfoisophthalic acid having a sulfo group. In addition, examples of the structure derived from a diol constituting the sulfonated polyester may include ethylene glycol, diethylene glycol, triethylene glycol, 1,4-cyclohexanedimethanol, 1,3-propanediol, 1,4-butanediol, 1,5-pentanediol, 1,6-hexanediol, 3-methyl-2,4-pentanediol, and 2-methyl-1,4-pentanediol. In addition, the sulfo group may form a salt with a metal ion of an alkali metal or the like, an ammonium ion, or the like. These sulfonated polyesters can be used singly or in combination of two or more kinds thereof.

In the present embodiment, a sulfonated copolyester of isophthalic acid is preferable from the viewpoint of washability of the cosmetic film. Furthermore, the sulfonated copolyester of isophthalic acid is more preferably a polyester of isophthalic acid, isophthalic acid having a sulfo group, and a diol compound containing diethylene glycol and/or 1,4-cyclohexanedimethanol.

It is possible to use commercially available products such as Eastman AQ38S Polymer, Eastman AQ55S Polymer, and Eastman AQ48 Ultra Polymer (manufactured by Eastman Chemical Japan Ltd.) as the sulfonated polyester.

The content of the component (A) in the water-based liquid cosmetic according to the present embodiment is from 2 to 11% by mass with respect to the total amount of the cosmetic, and preferably from 3 to 10% by mass and more preferably from 4 to 10% by mass from the viewpoint of water resistance and washability. Incidentally, it is difficult to obtain sufficient washability when the content of the component (A) is less than 2% by mass and it is difficult to obtain sufficient water resistance when it exceeds 11% by mass.

As the polymer containing, as a constitutional unit, an alkyl (meth)acrylate monomer of the component (B), it is possible to use, for example, an alkyl acrylate-styrene copolymer, an alkyl acrylate copolymer, an alkyl acrylate-diacetone acrylamide copolymer, an alkyl acrylate-vinyl acetate copolymer, an alkyl acrylate-acrylamide copolymer, an alkyl acrylate-octylacrylamide copolymer, and an alkyl acrylate-ammonium methacrylate copolymer. These can be used singly or in combination of two or more kinds thereof.

The copolymers described above may be blended in the water-based liquid cosmetic in the form of an emulsion.

The water-based liquid cosmetic according to the present embodiment contains preferably one or more kinds of an alkyl acrylate-styrene copolymer, an alkyl acrylate copolymer, or an alkyl acrylate-diacetone acrylamide copolymer and more preferably one or more kinds of an alkyl acrylate-styrene copolymer or an alkyl acrylate copolymer from the viewpoint of rub resistance, water resistance, and washability.

The content of the component (B) in the water-based liquid cosmetic according to the present embodiment is from 2 to 18% by mass with respect to the total amount of the cosmetic, and preferably from 3 to 15% by mass and more preferably from 5 to 15% by mass from the viewpoint of rub resistance, water resistance, and washability. Incidentally, it is difficult to obtain sufficient water resistance when the content of the component (B) is less than 2% by mass and it is difficult to obtain sufficient washability when it exceeds 18% by mass.

In addition, in the water-based liquid cosmetic according to the present embodiment, the mass ratio (A):(B) of the component (A) to the component (B) is preferably from 1:0.5 to 1:4 from the viewpoint of water resistance and washability.

In the water-based liquid cosmetic according to the present embodiment, it is possible to further blend another film-forming agent other than the component (A) and the component (B) in a range in which the effect of the invention of the present application is not impaired. Examples of such a film-forming agent may include polyvinylpyrrolidone, polyvinyl alcohol, carboxyvinyl polymer and any salt thereof, a vinyl acetate-vinyl pyrrolidone copolymer, hydroxypropyl methylcellulose, hydroxyethyl cellulose, carboxymethyl cellulose and any salt thereof, and any polyacrylate salt.

Examples of the coloring pigment to be blended in the water-based liquid cosmetic according to the present embodiment may include inorganic pigments such as carbon black, Prussian blue, red iron oxide, yellow iron oxide, black iron oxide, cobalt oxide, ultramarine, titanium oxide, zinc oxide, and charcoal, pearl pigments (mica titanium, fish scale foil, bismuth oxychloride, and the like), organic pigments (red No. 228, red No. 226, blue No. 404, and the like). It is also possible to use those obtained by subjecting these coloring pigments to a surface treatment by a known method using a silicone compound, a metal soap, an amino acid compound, or a fluorine compound.

The amount of the coloring pigment blended in the water-based liquid cosmetic according to the present embodiment may be 3% by mass or more with respect to the total amount of the cosmetic.

It is possible to further blend a dispersant in the water-based liquid cosmetic according to the present embodiment. As the dispersant, for example, a hydrophilic nonionic surfactant, an anionic surfactant, a cationic surfactant, and an amphoteric surfactant can be used. Examples of the hydrophilic nonionic surfactant may include a polyoxyalkylene alkyl ether, a glycerin alkyl ether, a glycerin fatty acid ester, a polyglycerin fatty acid ester, a sorbitan fatty acid ester and any alkylene glycol adduct thereof, a polyalkylene glycol fatty acid ester, polyglycerin-modified silicone, and polyether-modified silicone. Examples of the anionic surfactant may include an alkyl phosphate salt, a polyoxyalkylene alkyl ether phosphate salt, a sulfonate salt, an alkyl sulfate salt, and a polyaspartate salt. Examples of the cationic surfactant may include an alkyl amine salt and an alkyl trimethyl ammonium salt. Examples of the amphoteric surfactant may include lecithin, a carboxybetaine type amphoteric surfactant, a sulfobetaine type amphoteric surfactant, and an amino acid type amphoteric surfactant.

In a case in which the water-based liquid cosmetic according to the present embodiment contains carbon black and is used as an automatic pen type eyeliner cosmetic, it is preferable to blend a hydrophilic nonionic surfactant and it is more preferable to blend a polyoxyalkylene alkyl ether-based hydrophilic nonionic surfactant having an HLB of 11 or more.

The amount of dispersant blended in the water-based liquid cosmetic according to the present embodiment is preferably from 0.2 to 2.5% by mass, more preferably from 0.3 to 2.0% by mass, and even more preferably from 0.5 to 1.6% by mass with respect to the total amount of the cosmetic from the viewpoint of securing sufficient water resistance as well as sufficiently dispersing the coloring pigment (particularly carbon black).

The content of water in the water-based liquid cosmetic according to the present embodiment is not particularly limited, but for example, it may be 50% by mass or more with respect to the total amount of the cosmetic.

It is possible to contain a solvent other than water in the water-based liquid cosmetic according to the present embodiment. Examples of the solvent may include ethanol.

It is possible to appropriately blend other components, which are usually used in cosmetics, such as a humectant, an ultraviolet absorber, a preservative, vitamins, a cosmetic ingredient, an antioxidant, a perfume, and a pH adjusting agent if necessary, in addition to the components described above, in the water-based liquid cosmetic according to the present embodiment in a range in which the effect of the invention is not impaired.

The viscosity of the water-based liquid cosmetic according to the present embodiment at 25° C. is preferably from 2 to 50 mPa·s and more preferably from 5 to 30 mPa·s from the viewpoint of liquid discharge properties and usability such as density of drawn line. The effect of the invention is remarkably exerted and further it is possible to obtain optimum discharge properties at the time of being used as an automatic pen type cosmetic when the viscosity is in this range. The viscosity here means a value measured for a sample at 25° C. by the Brookfield rotational viscometer under a rotating condition of 12 rpm by a BL adapter and 1 minute.

The water-based liquid cosmetic according to the present embodiment can be produced by dissolving the film-forming agent, the coloring pigment, and water described above and other components if necessary and uniformly stirring and mixing the solution.

The water-based liquid cosmetic according to the present embodiment can be used as a make-up cosmetic such as eyeliner, eyebrow, or mascara.

The water-based liquid cosmetic according to the present embodiment can be utilized in a known product form used in cosmetic products. Examples of the product form may include an automatic pen type, a bottle type, and a mechanical pen that have an extrusion mechanism to extrude the cosmetic filled in the filling portion by a piston or the like, such as a dial type pen or a knock type pen. Among these, an automatic pen type is preferred from the viewpoint of a convenience of usage, portability, and favorable compatibility with a water-based liquid cosmetic. The automatic pen type cosmetics are equipped with a fiber bundle impregnated with a cosmetic or a filling portion filled with a cosmetic and an applying portion, and the cosmetic is discharged by the action of surface tension of the liquid cosmetic and capillary phenomenon.

EXAMPLES

Hereinafter, the invention will be more specifically described with reference to Examples, but the invention is not limited to the following Examples.

Production of Water-Based Liquid Cosmetic

Examples 1 to 16 and
Comparative Examples 1 to 16

The water-based liquid cosmetics were obtained by dissolving the respective components at the proportions (parts by mass) presented in Tables 1 to 4 and uniformly stirring and mixing the solution.

Incidentally, the following ones were used as the respective components presented in Tables 1 to 4.
Dispersant 1: Beheneth-30 (manufactured by Nikko Chemicals Co., Ltd., trade name: NIKKOL BB-30)
Dispersant 2: Laureth-4 (manufactured by Nikko Chemicals Co., Ltd., trade name: NIKKOL BL-4.2)
Dispersant 3: PEG-55 Stearate (manufactured by Nikko Chemicals Co., Ltd., trade name: NIKKOL MYS-55V)
Coloring pigment 1: Carbon black
Coloring pigment 2: Prussian blue
Film-forming agent A1: sulfonated polyester (manufactured by Eastman Chemical Japan Ltd., trade name: Eastman AQ55S Polymer)
Film-forming agent B1: Alkyl acrylate copolymer emulsion (manufactured by DAITO KASEI KOGYO CO., LTD., trade name: DAITOSOL 5000SJ, solid content: 50% by mass)
Film-forming agent B2: Alkyl acrylate-styrene copolymer emulsion (manufactured by DAITO KASEI KOGYO CO., LTD., trade name: DAITOSOL 5000STY, solid content: 50% by mass)
Film-forming agent B3: Alkyl acrylate-vinyl acetate copolymer emulsion (manufactured by Daido Chemical Industry Co., Ltd., trade name: VINYSOL 2140L, solid content: 45% by mass)
Film-forming agent B4: Alkyl acrylate-diacetone acrylamide copolymer emulsion (manufactured by GOO CHEMICAL CO., LTD., trade name: Plascize L-9540U, solid content: 40% by mass)

Film-forming agent C1: Sodium carboxymethyl cellulose (manufactured by DAICEL FINECHEM LTD., trade name: CMC Daicel)
Film-forming agent C2: Hydroxypropyl methyl cellulose (manufactured by Shin-Etsu Chemical Co., Ltd., trade name: METOLOSE 60SH-4000)
Film-forming agent C3: Polyvinyl pyrrolidone (manufactured by ISP Japan Co., Ltd., trade name: PVP K-30)

<Evaluation of Water-Based Liquid Cosmetic>

The water-based liquid cosmetic obtained above was filled in an automatic type container to produce a filled product.

The liquid discharge properties, density of drawn line, convenience of drawing (attachment to the skin), lasting properties (rub resistance, water resistance, sebum resistance), and washability of the filled product thus produced were evaluated in accordance with the following methods.

[Liquid Discharge Properties (Product Filled in Automatic Type Container)]

The filled product was applied to the skin and the liquid discharge properties were evaluated in three ranks.

(Evaluation Criteria)
◯: it is discharged without any problem
Δ: it is discharged but insufficient
x: it is not discharged

[Density of Drawn Line and Convenience of Drawing]

The filled product was evaluated by 10 professional panelists for cosmetic evaluation for each of the evaluation items of the "density of drawn line" and the "convenience of drawing" and scored in five ranks in accordance with the following evaluation criteria by each of the panelists, further the scores of the respective panelists thus obtained were averaged, and each of the evaluation items was judged in four ranks based on the average point and the following criteria.

(Criteria)
⊙: average point is 4.5 points or more
◯: average point is 3.5 points or more and less than 4.5 points
Δ: average point is 1.5 points or more and less than 3.5 points
x: average point is less than 1.5 points (Evaluation Criteria on Density of Drawn Line)
5 points: significantly favorable (significantly sufficient density)
4 points: favorable (enough density)
3 points: neither favorable nor poor (not sufficient density but practically no problem)
2 points: slightly poor (slightly thin and practically a little problem)
1 point: poor (thin and practically a problem)

(Evaluation Criteria on Convenience of Drawing (Attachment to the Skin))
5 points: significantly favorable (significantly easy to draw)
4 points: favorable (easy to draw)
3 points: neither favorable nor poor (little bleeding but practically no problem)
2 points: slightly poor (slightly bleeding and practically a little problem)
1 point: poor (greatly bleeding and practically a problem)

[Rub Resistance]

A line was drawn on the arm with the filled product and allowed to dry for 10 minutes. The applied portion was rubbed with a dry cotton swab 10 times, and the removal degree of the applied portion was visually observed and evaluated in four ranks in accordance with the following evaluation criteria.

(Evaluation Criteria on Rub Resistance)
⊙: significantly favorable (applied portion is not peeled off at all to be significantly favorable)
◯: favorable (little of applied portion is peeled off to be favorable)
Δ: slightly poor (applied portion is partially peeled off or spread with slightly bleeding)
x: poor (applied portion is mostly peeled off or spread with bleeding)

[Water Resistance]

A line was drawn on the arm with the filled product and allowed to dry for 10 minutes. The applied portion was rubbed with the ball of the finger several times in running water, and the remaining degree of the applied portion was visually observed and evaluated in four ranks in accordance with the following evaluation criteria.

(Evaluation Criteria on Water Resistance)
⊙: applied portion is not peeled off even when being rubbed back and forth 20 times
◯: applied portion is peeled off when being rubbed back and forth 15 times
Δ: applied portion is peeled off when being rubbed back and forth 10 times
x: applied portion is peeled off when being rubbed back and forth 5 times

[Sebum Resistance]

A line was drawn on the arm with the filled product and allowed to dry for 10 minutes. Artificial sebum (squalane) was dropped on the applied portion, a Kleenex was pressed thereon, and the degree of transfer of the applied portion to the Kleenex was visually observed and evaluated in four ranks in accordance with the following evaluation criteria.

(Evaluation Criteria on Sebum Resistance)
⊙: significantly favorable (applied portion is not transferred at all)
◯: favorable (little of applied portion is transferred)
Δ: slightly poor (applied portion is slightly transferred)
x: poor (applied portion is transferred)

[Washability]

A line was drawn on the arm with the filled product and allowed to dry for 10 minutes. The removal degree of the applied portion was visually observed using hot water or soap and evaluated in four ranks in accordance with the following evaluation criteria.

(Evaluation Criteria on Washability)
⊙: significantly favorable (applied portion is clearly removed with hot water or soap)
◯: favorable (applied portion is removed with hot water or soap)
Δ: slightly poor (little of applied portion remains)
x: poor (applied portion remains)

TABLE 1

|  | Example 1 | Example 2 | Example 3 | Example 4 | Example 5 | Example 6 | Example 7 | Example 8 | Example 9 |
| --- | --- | --- | --- | --- | --- | --- | --- | --- | --- |
| Water | 54.04 | 59.08 | 54.07 | 59.10 | 50.61 | 66.62 | 58.12 | 46.12 | 53.12 |
| Butylene glycol | 8.50 | 8.50 | 8.50 | 8.50 | 8.50 | 8.50 | 8.50 | 8.50 | 8.50 |
| Ethanol | 5.00 | 5.00 | 5.00 | 5.00 | 5.00 | — | 3.00 | 3.00 | 3.00 |
| Dispersant 1 | 0.55 | 0.55 | 0.55 | 0.55 | — | 0.55 | 0.55 | 0.55 | 0.55 |
| Dispersant 2 | — | — | — | — | 0.75 | — | — | — | — |

TABLE 1-continued

|  | Example 1 | Example 2 | Example 3 | Example 4 | Example 5 | Example 6 | Example 7 | Example 8 | Example 9 |
|---|---|---|---|---|---|---|---|---|---|
| Coloring pigment 1 (carbon black) | 6.00 | 6.00 | 6.00 | 6.00 | 6.00 | 6.00 | 6.00 | 6.00 | 6.00 |
| Coloring pigment 2 (Prussian blue) | — | — | — | — | — | — | — | — | — |
| Film-forming agent A1 | 5.00 | 10.00 | 5.00 | 10.00 | 4.65 | 5.00 | 3.00 | 5.00 | 8.00 |
| Film-forming agent B1 (solid content: 50% by mass) | 20.00 | 10.00 | — | — | — | — | — | — | — |
| Film-forming agent B2 (solid content: 50% by mass) | — | — | 20.00 | 10.00 | 20.00 | — | 20.00 | 30.00 | 20.00 |
| Film-forming agent B3 (solid content: 45% by mass) | — | — | — | — | — | — | — | — | — |
| Film-forming agent B4 (solid content: 40% by mass) | — | — | — | — | — | 12.50 | — | — | — |
| Film-forming agent C1 | — | — | — | — | — | — | — | — | — |
| Film-forming agent C2 | — | — | — | — | — | — | — | — | — |
| Film-forming agent C3 | — | — | — | — | 3.60 | — | — | — | — |
| pH adjusting agent | 0.08 | 0.04 | 0.05 | 0.02 | 0.04 | — | — | — | — |
| Preservative | 0.83 | 0.83 | 0.83 | 0.83 | 0.85 | 0.83 | 0.83 | 0.83 | 0.83 |
| Sum | 100.00 | 100.00 | 100.00 | 100.00 | 100.00 | 100.00 | 100.00 | 100.00 | 100.00 |
| Liquid discharge properties | ○ | ○ | ○ | ○ | ○ | ○ | ○ | ○ | ○ |
| Density of drawn line | ◎ | ◎ | ◎ | ◎ | ◎ | ○ | ◎ | ◎ | ◎ |
| Convenience of drawing (attachment to skin) | ◎ | ◎ | ◎ | ◎ | ◎ | ◎ | ◎ | ◎ | ◎ |
| Rub resistance | ◎ | ○ | ◎ | ○ | ◎ | ○ | ○ | ◎ | ○ |
| Water resistance | ◎ | ○ | ◎ | ○ | ◎ | ○ | ◎ | ◎ | ○ |
| Sebum resistance | ◎ | ◎ | ◎ | ◎ | ◎ | ◎ | ◎ | ◎ | ◎ |
| Washability | ○ | ○ | ○ | ○ | ◎ | ○ | ○ | ○ | ◎ |

TABLE 2

|  | Example 10 | Example 11 | Example 12 | Example 13 | Example 14 | Example 15 | Example 16 |
|---|---|---|---|---|---|---|---|
| Water | 49.08 | 53.91 | 51.85 | 50.65 | 51.25 | 51.77 | 54.23 |
| Butylene glycol | 8.50 | 8.50 | 8.50 | 8.50 | 8.50 | 8.50 | 8.50 |
| Ethanol | 5.00 | 3.00 | 3.00 | 3.00 | 3.00 | 5.00 | 3.00 |
| Dispersant 1 | 0.55 | 0.73 | 0.91 | 1.09 | 1.51 | 0.55 | — |
| Dispersant 2 | — | — | — | — | — | — | — |
| Coloring pigment 1 (carbon black) | 6.00 | 8.00 | 10.00 | 12.00 | 10.00 | 6.00 | — |
| Coloring pigment 2 (Prussian blue) | — | — | — | — | — | — | 10.00 |
| Film-forming agent A1 | 10.00 | 5.00 | 5.00 | 4.00 | 5.00 | 5.00 | 3.52 |
| Film-forming agent B1 (solid content: 50% by mass) | — | — | — | — | — | — | — |
| Film-forming agent B2 (solid content: 50% by mass) | 20.00 | 20.00 | 20.00 | 20.00 | 20.00 | — | 20.00 |
| Film-forming agent B3 (solid content: 45% by mass) | — | — | — | — | — | 22.30 | — |
| Film-forming agent B4 (solid content: 40% by mass) | — | — | — | — | — | — | — |
| Film-forming agent C1 | — | — | — | — | — | — | — |
| Film-forming agent C2 | — | — | — | — | — | — | — |
| Film-forming agent C3 | — | — | — | — | — | — | — |
| pH adjusting agent | 0.04 | — | — | — | — | 0.05 | — |
| Preservative | 0.83 | 0.86 | 0.74 | 0.76 | 0.74 | 0.83 | 0.75 |
| Sum | 100.00 | 100.00 | 100.00 | 100.00 | 100.00 | 100.00 | 100.00 |
| Liquid discharge properties | ○ | ○ | ○ | ○ | ○ | ○ | ○ |
| Density of drawn line | ◎ | ◎ | ◎ | ◎ | ◎ | ○ | ○ |
| Convenience of drawing (attachment to skin) | ◎ | ◎ | ◎ | ◎ | ◎ | ◎ | ◎ |
| Rub resistance | ○ | ○ | ○ | ○ | ○ | ○ | ○ |
| Water resistance | ○ | ◎ | ◎ | ◎ | ○ | ○ | ◎ |

TABLE 2-continued

|  | Example 10 | Example 11 | Example 12 | Example 13 | Example 14 | Example 15 | Example 16 |
|---|---|---|---|---|---|---|---|
| Sebum resistance | ⊙ | ⊙ | ⊙ | ⊙ | ⊙ | ⊙ | ○ |
| Washability | ○ | ○ | ○ | ○ | ⊙ | ○ | ○ |

TABLE 3

|  | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Water | 67.47 | 57.39 | 57.43 | 55.09 | 57.47 | 75.27 | 75.27 | 69.02 | 74.07 |
| Butylene glycol | 8.50 | 8.50 | 8.50 | 8.50 | 8.50 | 8.50 | 8.50 | 8.50 | 8.50 |
| Ethanol | 5.00 | 5.00 | 5.00 | 5.00 | — | 5.00 | 5.00 | 5.00 | 5.00 |
| Dispersant 1 | 2.20 | 2.20 | 2.20 | 2.20 | 2.20 | 2.20 | 2.20 | 0.55 | 0.55 |
| Dispersant 2 | — | — | — | — | — | — | — | — | — |
| Coloring pigment 1 (carbon black) | 6.00 | 6.00 | 6.00 | 6.00 | 6.00 | 6.00 | 6.00 | 6.00 | 6.00 |
| Coloring pigment 2 (Prussian blue) | — | — | — | — | — | — | — | — | — |
| Film-forming agent A1 | 10.00 | — | — | — | — | — | — | 10.00 | 5.00 |
| Film-forming agent B1 (solid content: 50% by mass) | — | 20.00 | — | — | — | — | — | — | — |
| Film-forming agent B2 (solid content: 50% by mass) | — | — | 20.00 | — | — | — | — | — | — |
| Film-forming agent B3 (solid content: 45% by mass) | — | — | — | 22.30 | — | — | — | — | — |
| Film-forming agent B4 (solid content: 40% by mass) | — | — | — | — | 25.00 | — | — | — | — |
| Film-forming agent C1 | — | — | — | — | — | 2.20 | — | 0.10 | — |
| Film-forming agent C2 | — | — | — | — | — | — | 2.20 | — | 0.05 |
| Film-forming agent C3 | — | — | — | — | — | — | — | — | — |
| pH adjusting agent | — | 0.08 | 0.04 | 0.08 | — | — | — | — | — |
| Preservative | 0.83 | 0.83 | 0.83 | 0.83 | 0.83 | 0.83 | 0.83 | 0.83 | 0.83 |
| Sum | 100.00 | 100.00 | 100.00 | 100.00 | 100.00 | 100.00 | 100.00 | 100.00 | 100.00 |
| Liquid discharge properties | ○ | ○ | ○ | ○ | X | X | X | ○ | ○ |
| Density of drawn line | Δ | ⊙ | ⊙ | ⊙ | Unevaluable | Unevaluable | Unevaluable | Δ | Δ |
| Convenience of drawing (attachment to skin) | ○ | ○ | ○ | ○ | Unevaluable | Unevaluable | Unevaluable | Δ | Δ |
| Rub resistance | Δ | ○ | ○ | Δ | Unevaluable | Unevaluable | Unevaluable | X | X |
| Water resistance | Δ | ⊙ | ⊙ | Δ | Unevaluable | Unevaluable | Unevaluable | X | X |
| Sebum resistance | ⊙ | ⊙ | ⊙ | ○ | Unevaluable | Unevaluable | Unevaluable | ⊙ | ⊙ |
| Washability | ⊙ | X | X | Δ | Unevaluable | Unevaluable | Unevaluable | ⊙ | ○ |

TABLE 4

|  | Comparative Example 10 | Comparative Example 11 | Comparative Example 12 | Comparative Example 13 | Comparative Example 14 | Comparative Example 15 | Comparative Example 16 |
|---|---|---|---|---|---|---|---|
| Water | 70.12 | 60.12 | 74.12 | 36.12 | 69.12 | 49.12 | 56.54 |
| Butylene glycol | 8.50 | 8.50 | 8.50 | 8.50 | 8.50 | 8.50 | 8.50 |
| Ethanol | 3.00 | 3.00 | 3.00 | 3.00 | 3.00 | 3.00 | 3.00 |
| Dispersant 1 | 0.55 | 0.55 | 0.55 | 0.55 | 0.55 | 0.55 | — |
| Dispersant 2 | — | — | — | — | — | — | — |
| Dispersant 3 | — | — | — | — | — | — | 1.00 |
| Coloring pigment 1 (carbon black) | 6.00 | 6.00 | 6.00 | 6.00 | 6.00 | 6.00 | — |
| Coloring pigment 2 (Prussian blue) | — | — | — | — | — | — | 10.00 |
| Film-forming agent A1 | 1.00 | 1.00 | 5.00 | 5.00 | 10.00 | 12.00 | — |

TABLE 4-continued

| | Comparative Example 10 | Comparative Example 11 | Comparative Example 12 | Comparative Example 13 | Comparative Example 14 | Comparative Example 15 | Comparative Example 16 |
|---|---|---|---|---|---|---|---|
| Film-forming agent B1 (solid content: 50% by mass) | — | — | — | — | — | — | 20.00 |
| Film-forming agent B2 (solid content: 50% by mass) | 10.00 | 20.00 | 2.00 | 40.00 | 2.00 | 20.00 | — |
| Film-forming agent B3 (solid content: 45% by mass) | — | — | — | — | — | — | — |
| Film-forming agent B4 (solid content: 40% by mass) | — | — | — | — | — | — | — |
| Film-forming agent C1 | — | — | — | — | — | — | — |
| Film-forming agent C2 | — | — | — | — | — | — | — |
| Film-forming agent C3 | — | — | — | — | — | — | — |
| pH adjusting agent | — | — | — | — | — | — | 0.15 |
| Preservative | 0.83 | 0.83 | 0.83 | 0.83 | 0.83 | 0.83 | 0.81 |
| Sum | 100.00 | 100.00 | 100.00 | 100.00 | 100.00 | 100.00 | 100.00 |
| Liquid discharge properties | ○ | ○ | ○ | ○ | ○ | ○ | ○ |
| Density of drawn line | ⊙ | ⊙ | ⊙ | ⊙ | Δ | ⊙ | ○ |
| Convenience of drawing (attachment to skin) | ○ | ⊙ | ○ | ⊙ | ○ | ⊙ | ○ |
| Rub resistance | Δ | ○ | Δ | ⊙ | ○ | ○ | Δ |
| Water resistance | ⊙ | ⊙ | X | ⊙ | X | Δ | ⊙ |
| Sebum resistance | ⊙ | ⊙ | ⊙ | ⊙ | ⊙ | ⊙ | ○ |
| Washability | X | X | ⊙ | Δ | ⊙ | ○ | ○ |

Example 17

Bottle Type

| (Component) | (Blending proportion (% by mass) |
|---|---|
| 1. Water | 52.75 |
| 2. Butylene glycol | 8.50 |
| 3. Ethanol | 3.00 |
| 4. Laureth-4 | 1.00 |
| 5. Carbon black | 8.00 |
| 6. Film-forming agent A1 described above | 6.20 |
| 7. Film-forming agent B2 described above (solid content: 50% by mass) | 15.00 |
| 8. Film-forming agent C3 described above | 4.80 |
| 9. Preservative described above | 0.75 |

The water-based liquid cosmetic was obtained by dissolving the components 1 to 9 and uniformly stirring and mixing the solution. This cosmetic was filled in a bottle container to produce bottle type eyeliner.

<Evaluation>

The eyeliner thus obtained was subjected to the same evaluation as above (liquid discharge is excluded), and the results were as follows. The density of drawn line was "⊙", the convenience of drawing (attachment to the skin) was "⊙", the rub resistance was "⊙", the water resistance was "⊙", the sebum resistance was "⊙", and the washability was "⊙".

The invention claimed is:

1. A water-based liquid cosmetic consisting essentially of a film-forming agent, a coloring pigment, and water, wherein
a sulfonated polyester (A) and a polymer (B) containing an alkyl (meth)acrylate monomer as a constitutional unit are contained at from 2 to 11% by mass and from 2 to 18% by mass with respect to a total amount of the cosmetic, respectively, as the film-form ing agent.

2. The water-based liquid cosmetic according to claim 1, wherein a sulfonated copolyester of isophthalic acid is contained as the component (A).

3. The water-based liquid cosmetic according to claim 1, wherein one or more kinds of an alkyl acrylate-styrene copolymer, an alkyl acrylate copolymer, or an alkyl acrylate-diacetone acrylamide copolymer is contained as the component (B).

4. The water-based liquid cosmetic according to claim 2, wherein one or more kinds of an alkyl acrylate-styrene copolymer, an alkyl acrylate copolymer, or an alkyl acrylate-diacetone acrylamide copolymer is contained as the component (B).

5. The water-based liquid cosmetic according to claim 1, wherein the sulfonated polyester (A) and polymer (B) containing an alkyl (meth)acrylate monomer as a constitutional unit are contained at from 3 to 10% by mass and from 3 to 15% by mass with respect to a total amount of the cosmetic, respectively, as the film-forming agent.

* * * * *